(12) United States Patent
Baumgartner et al.

(10) Patent No.: US 12,305,149 B2
(45) Date of Patent: May 20, 2025

(54) ORGANIC COMPOUNDS

(71) Applicant: Givaudan SA, Vernier (CH)

(72) Inventors: Corinne Baumgartner, Hinwil (CH);
Felix Flachsmann, Duebendorf (CH);
Nathalie Joset, Duebendorf (CH);
Veronika Magdalena Zelenay,
Kemptthal (CH)

(73) Assignee: Givaudan SA, Vernier (CH)

( * ) Notice: Subject to any disclaimer, the term of this patent is extended or adjusted under 35 U.S.C. 154(b) by 756 days.

(21) Appl. No.: 17/606,640

(22) PCT Filed: May 7, 2019

(86) PCT No.: PCT/EP2019/061708
§ 371 (c)(1),
(2) Date: Oct. 26, 2021

(87) PCT Pub. No.: WO2020/224767
PCT Pub. Date: Nov. 12, 2020

(65) Prior Publication Data
US 2022/0235296 A1 Jul. 28, 2022
US 2023/0212482 A9 Jul. 6, 2023

(51) Int. Cl.
*C11D 3/26* (2006.01)
*C07C 45/32* (2006.01)
*C07C 323/52* (2006.01)
*C11D 3/00* (2006.01)
*C11D 3/34* (2006.01)
*C11D 3/50* (2006.01)

(52) U.S. Cl.
CPC .............. *C11D 3/50* (2013.01); *C07C 45/32* (2013.01); *C07C 323/52* (2013.01); *C11D 3/001* (2013.01); *C11D 3/349* (2013.01); *C11D 2111/12* (2024.01)

(58) Field of Classification Search
CPC .. C11D 3/001; C11D 3/26; C11D 3/34; C11D 3/349; C11D 3/50; C11D 11/0017; C07C 323/52; C07C 45/32
See application file for complete search history.

(56) References Cited

U.S. PATENT DOCUMENTS

2010/0179088 A1* 7/2010 Flachsmann .......... C07C 323/58
560/118
2014/0323383 A1 10/2014 Trujillo et al.

FOREIGN PATENT DOCUMENTS

| CN | 104761442 | * | 11/2017 | .......... C07C 49/543 |
| CN | 104761442 A | | 11/2017 | |
| WO | 0135768 A1 | | 5/2001 | |
| WO | WO 01/35768 | * | 5/2001 | .............. A23L 3/34 |
| WO | 03049666 A2 | | 6/2003 | |
| WO | 2008154765 A1 | | 12/2008 | |
| WO | 2012113746 A1 | | 8/2012 | |
| WO | 2016131694 A1 | | 8/2016 | |

OTHER PUBLICATIONS

International Search Report for Application No. PCT/EP2019/061708 dated Jan. 2, 2020.
Written Opinion for Application No. PCT/EP2019/061708 dated Jan. 2, 2020.

* cited by examiner

*Primary Examiner* — Brian P Mruk
(74) *Attorney, Agent, or Firm* — Curatolo Sidoti & Trillis Co., LPA; Floyd Trillis, III; Salvatore A. Sidoti

(57) ABSTRACT

The present invention relates to compounds of formula (I) as herein defined, capable of releasing fragrant compounds in a controlled manner into the surroundings. The present invention is also concerned with a process for their production, and consumer products comprising them.

5 Claims, No Drawings

ORGANIC COMPOUNDS

CROSS REFERENCE TO RELATED APPLICATIONS

This application is a national stage application of International Application No. PCT/EP2019/061708, filed 7 May 2019, which is incorporated herein by reference.

The present invention relates to a particular class of compounds capable of releasing fragrant compounds in a controlled manner into the surroundings. The present invention is also concerned with a process for their production, and consumer products comprising them. In particularly the present invention relates to precursors that release damascone.

Damascone

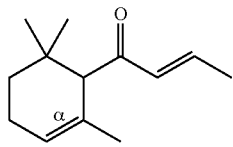

DAMASCONE ALPHA

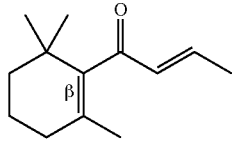

DAMASCONE BETA

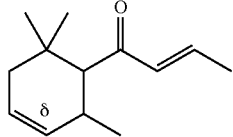

DAMASCONE DELTA respectively, 1-(2',6',6'-trimethylcyclohex-2'-en-1'-yl)but-2-en-1-one, 1-(2',6',6'-trimethylcyclohex-1'-en-1'-yl)but-2-en-1-one and 1-(2',6',6'-trimethylcyclohex-3'-en-1'-yl)but-2-en-1-one is a family of desirable fragrance ingredients that occur in essential oils. They are frequently used in perfumery.

There is interest in providing a damascone precursor, that is, a compound that is itself, basically because of the high molecular weight, essentially odorless, but which, in particular circumstances, will decompose to release damascone at a desired time.

It has now been found that the compound of formula (I) as herein below described can act as precursor for the release, by spontaneous air oxidation, of damascone.

Similar compounds are known from International Publication WO 01/35768, in which certain carbonyl compounds, including damascone, may be reacted with cysteine to provide flavouring products. However, these compounds are not precursors, but integral flavouring materials.

Thus, there is provided in one aspect the use of a compound of formula (I)

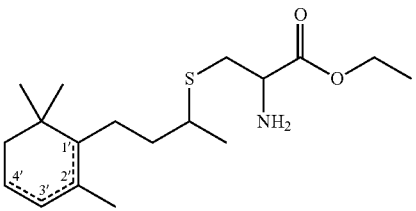

as precursor for generating, by spontaneous air oxidation, a damascone of formula (II)

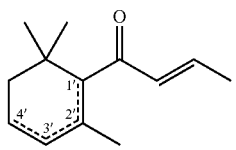

wherein one of the dotted lines represents together with the carbon-carbon bond a double bond and each of the other two dotted lines represent together with the carbon-carbon bond a single bond.

In one preferred embodiment the compound of formula (I) is a compound wherein the dotted line between C3' and C4' represents together with the carbon-carbon bond a double bond (i.e. the compound of formula (I) is ethyl S-(4-oxo-4-(2',6',6'-trimethylcyclohex-3'-en-1'-yl)butan-2-yl)cysteinate).

The activating conditions, which lead to the cleavage step, comprise the presence of molecular oxygen. The concentration of oxygen in the air is sufficient for cleaving the compound of formula (I) in such a way, that the cleavage products can be detected in the ambient air, e.g. by olfaction or GC-MS analysis of headspace samples.

The compounds of formula (I) are very stable when not exposed to the ambient air, i.e. when stored neat or in a diluent conventionally used in conjunction with odorants, such as dipropyleneglycol (DPG), isopropylmyristate (IPM), triethylcitrate (TEC), pentane-1,2-diol, and alcohol (e.g. ethanol), and known odorants. Very good storage stability has been proven also when incorporated in consumer products such as detergent, shampoo and fabric conditioner. Thus the compounds of formula (I) may find use in a broad range of consumer products in which a prolonged and defined release of fragrant compounds is desired.

In one specific embodiment the compounds of formula (I) are useful in consumer products, such as detergent products, including powder and liquid detergents or detergents in form of tablets, pouches/single unit doses, soap and laundry bars, fabric conditioner, including tumble dryer sheets, and scent boosters (liquid or solid).

In another specific embodiment the compounds of formula (I) are useful in cosmetic products, which include (a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

Thus, there is provided in a further aspect of the present invention, a consumer product comprising a compound of formula (I) and a product base.

As used herein, 'consumer product base' means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like.

In one embodiment the compounds of formula (I) are especially useful as part of fragrances to be used in laundry products, in which they can release damascone upon usage. However, under certain conditions the odor profile is perceived as fruity berry with a slightly plastic off-note. Surprisingly it was found that when combined with a second class of compounds, a combination is obtained which results in an odor profile which is essentially free of the undesirable plastic note.

Thus there is provided in a further aspect of the present invention, a combination of the compound of formula (I) with a compound of formula (III)

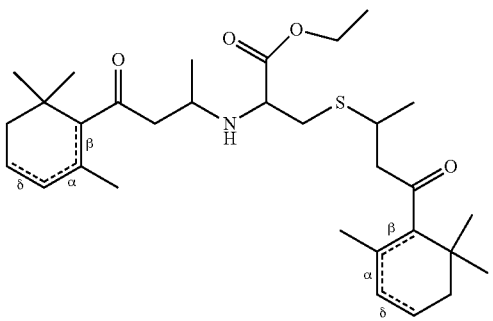

(III)

wherein the dotted lines represents a double bond located at one of the alpha-, beta- or delta-positions on each of the cyclohexene rings. These compounds, which are bis-adducts, are described in International Publication WO 2008/154765.

It was found that, when a combination of a compound of formula (I) with a compound of formula (III) was used in laundry products, that the deposition rate is enhanced.

It was also found, when a combination of a compound of formula (I) with a compound of formula (III) was used, that a continuous release of compounds of formula (II) is noticeable from an early stage to several days (e.g. when used in a detergent product, already on wet fabric).

In one preferred embodiment the compound of formula (III) is a compound wherein the dotted lines represents a double bond located in delta position on each of the cyclohexane rings (i.e. the compound of formula (III) is ethyl N,S-bis(4-oxo-4-(2',6',6'-trimethylcyclohex-3'-en-1'-yl)butan-2-yl)cysteinate))

In another preferred embodiment there is provided a mixture of a compound of formula (I) and a compound of formula (III) in a ratio of 1:40 to 40:1, including a ratio of 1:20 to 1:10, e.g. 1:15 to 1:11.

In one particular embodiment there is provided a mixture of ethyl S-(4-oxo-4-(2',6',6'-trimethylcyclohex-3'-en-1'-yl) butan-2-yl)cysteinate and ethyl N,S-bis(4-oxo-4-(2',6',6'-trimethylcyclohex-3'-en-1'-yl)butan-2-yl)cysteinate), preferably at a ratio of 1:40 to 40:1, including a ratio of 1:20 to 1:10, e.g. 1:15 to 1:11.

The compounds of formula (I), or a mixture of a compound of formula (I) and a compound of formula (III), can be used alone, or in combination with other fragrance ingredients and/or precursors thereof. Such fragrance ingredients are described, for example, in "Perfume and Flavor Chemicals", S. Arctander, Ed., Vol. I & II, Allured Publishing Corporation, Carol Stream, USA, 2003 and include fragrance compounds of natural or synthetic origin and essential oils.

The following list comprises examples of known fragrance ingredients, which may be combined with the compounds of formula (I):

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); delta Damascone ((2E)-1-(2,6,6-trimethylcyclohex-2-en-1-yl)but-2-en-1-one); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In one particular embodiment the compound of formula (I), or the mixture of a compound of formula (I) and a compound of formula (III), may be used in combination with other fragrance precursors, including 1-butoxy-3-((1E,4Z)-hepta-1,4-dien-1-yl)benzene, (4-(dodecylthio)-4-methylpentan-2-one, 2-ethoxy-4-((1E,4Z)-hepta-1,4-dien-1-yl)phenol, and ethyl 2-acetyl-4-methyltridec-2-enoate.

The amounts in which the compounds of formula (I), or the mixture of a compound of formula (I) and the compound of formula (III), may be incorporated in the various consumer products vary within a wide range. The amounts depend on the nature of the product to which the compounds of formula (I), or the mixture of a compound of formula (I) and the compound of formula (III), are added and the desired olfactory effect. The amounts used also depend on the co-ingredients in a given composition when the compounds of formula (I), or the mixture of a compound of formula (I) and the compound of formula (III), are used in admixture with perfuming co-ingredients, solvents or adjuvants. Typical concentrations are from 0.0001 to 5 weight percent of the article. In one embodiment, compounds of the present invention may be employed in a fabric softener in an amount of from 0.0001 to 2 weight percent. In another embodiment, compounds of the present invention may be employed in a detergent in an amount of from 0.0001 to 4 weight percent. In another embodiment, compounds of the present invention may be used in fine perfumery in amounts from 0.001 to 10 weight percent (e.g. up to about 5 weight percent), more preferably between 0.02 and 4 weight percent. However, these values are given only by way of example, since the experienced perfumer may also achieve effects or may create novel accords with lower or higher concentrations.

The compounds of formula (I) are novel in its own right. Thus there is provided in a further aspect of the invention a compound of formula (I)

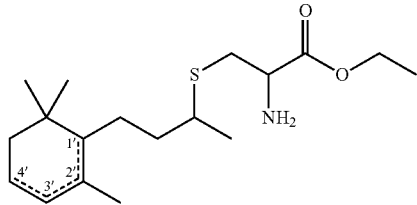

wherein one of the dotted lines represents together with the carbon-carbon bond a double bond and each of the other two dotted lines represent together with the carbon-carbon bond a single bond.

The compounds of formula (I) may be prepared by a 1,4 addition of cysteine-ethyl ester to damascone in a suitable solvent such as tetrahydrofuran, dimethyl formamide, ethanol or water and in the presence of an organic or inorganic base, such as N-ethyldiisopropylamine, triethylamine, potassium or sodium carbonate or hydroxide.

Other conditions for the formation of thioethers can be employed which are known to the person skilled in the art of organic synthesis.

The mixture of a compound of formula (I) and a compound of formula (III) may be either prepared by admixing the two compounds in the desired ratio after each of them was prepared independently of each other. Alternatively, the mixture can be prepared in situ, e.g., by following the process as described in the Examples.

The invention is now further described with reference to the following non-limiting examples. These examples are for the purpose of illustration only and it is understood that variations and modifications can be made by one skilled in the art.

Example 1: Ethyl S-(4-oxo-4-(2',6',6'-trimethylcyclohex-3'-en-1'-yl)butan-2-yl) cysteinate In a 250 mL two-neck round-bottom flask were placed (E)-1-(2',6',6'-trimethylcyclohex-3'-en-1'-yl)but-2-en-1-one (10 g, 52.0 mmol) and L-cysteine ethyl ester hydrochloride (15 g, 81 mmol) in water (100 ml). Under stirring at room temperature, potassium carbonate (8 g, 57.9 mmol) was added in one portion and the resulting mixture was stirred overnight at room temperature. MTBE (50 ml) was added to the mixture which was then stirred for an additional hour. The mixture was transferred to a separatory funnel, the phases were separated and the aq. phase was extracted with MTBE (2×50 ml). The org. phases were combined and washed with water (3×50 ml), water/brine (20 ml/30 ml) and brine (50 ml), dried over MgSO$_4$, filtered and the solvent was evaporated to give ethyl S-(4-oxo-4-(2',6',6'-trimethylcyclohex-3'-en-1'-yl)butan-2-yl)-L-cysteinate (16.91 g, 49.5 mmol, 95% yield) as a mixture of four isomers and as a light yellow oil.

Odor description (dry-down of a 10% DPG solution after 24 hours on a smelling strip): fruity berry, reminiscent of stewed apple, slightly plastic, chemical.

$^1$H NMR (CDCl$_3$, 400 MHz): δ=5.57-5.51 (m, 1H), 5.44 (br d, J=10 Hz, 1H), 4.20 (br q, J=7.1 Hz, 2H), 3.71-3.63 (m, 1H), 3.38-3.30 (m, 1H), 3.00-2.88 (m, 1.5H), 2.83-2.77 (m, 1H), 2.73-2.71 (m, 1H), 2.56-2.48 (m, 1.5H), 2.22 (d, J=10.5 Hz, 0.5H), 2.21 (d, J=10.6 Hz, 0.5H), 1.97 (br d, J=17.6 Hz, 1H), 1.8 (br s, 2H), 1.70 (br d, J=17.6 Hz, 1H), 1.32-1.30 (m, 3H), 1.29 (t, J=7.1 Hz, 3H), 1.01-0.87 (m, 9H) ppm.

$^{13}$C-NMR (CDCl$_3$, 100 MHz): δ=211.91, 211.80, 173.76, 131.59, 131.57, 131.51, 131.48, 124.04, 123.92, 123.9, 62.67, 62.64, 62.59, 61.00, 60.97, 55.03, 54.91, 54.89, 54.82, 54.32, 54.30, 54.06, 41.53, 41.50, 36.07, 36.03, 35.93, 35.86, 34.71, 34.67, 34.41, 32.97, 32.94, 32.92, 32.87, 31.57, 31.52, 31.43, 31.38, 29.65, 29.61, 29.58, 21.76, 21.74, 21.56, 21.50, 20.55, 20.53, 19.73, 19.68 ppm.

MS (EI, 70 eV): 341 ([M]$^{+•}$, 2), 123 (67), 117 (69), 102 (65), 81 (51), 76 (49), 75 (80), 69 (100), 43 (60), 41 (58), 29 (56).

Example 2: Ethyl S-(4-oxo-4-(2',6',6'-trimethylcyclohex-3'-en-1'-yl)butan-2-yl) cysteinate (GR-87-1182-2) and Ethyl N,S-bis(4-oxo-4-(2',6',6'-trimethylcyclohex-3'-en-1'-yl)butan-2-yl)cysteinate)

In a 1500 mL sulfonation flask were placed (E)-1-(2',6',6'-trimethylcyclohex-3'-en-1'-yl)but-2-en-1-one (200 g, 1.04 mol) and L-cysteine ethyl ester hydrochloride (98.1 g, 0.53 mol) in water (520 ml). Under stirring at room temperature, potassium carbonate (72.16 g, 0.52 mol) was added in one portion. The reaction mixture was then stirred overnight at room temperature. The solution was transferred into a separatory funnel, MTBE (100 ml) was added, the phases were separated and the aq. phase was extracted with MTBE (100 ml). The org. phases were combined and washed with brine (250 ml), dried over MgSO$_4$, filtered and the solvent was evaporated to give a clear yellow oil containing a mixture of isomers of S-(4-oxo-4-(2',6',6'-trimethylcyclohex-3'-en-1'-yl)butan-2-yl)-L-cysteinate and isomers of ethyl N,S-bis(4-oxo-4-(2',6',6'-trimethylcyclohex-3'-en-1'-yl)butan-2-yl)-L-cysteinate in a ratio of 1:14 (255.39 g, 0.48 mol, 92% yield)

Odor description of the obtained mixture (dry-down of a 10% DPG solution after 24 hours on a smelling strip): fruity, damascone like, stewed apple, clean, pleasant The activating conditions to release compounds of formula II comprise a combination of change of pH, elevated temperature and exposure to air. The combination of trigger conditions has the advantage of continuous release of odoriferous compounds of formula II from an early stage (e.g. on wet fabric in detergent application) to several days.

Example 3: Ethyl N-(4-oxo-4-(2,6,6-trimethylcyclohex-3-en-1-yl)but-2-en-2-yl)-S-(4-oxo-4-(2,6,6-trimethylcyclohex-3-en-1-yl)butan-2-yl)cysteinate)

Step 1: In a 250 ml sulfonation flask surmounted by a dean-stark, 3-hydroxy-1-(2,6,6-trimethylcyclohex-3-en-1-yl)but-2-en-1-onediketone (5.1 g, 24.5 mmol) and L-cysteine ethyl ester hydrochloride (4.46 g, 24 mmol) were suspended in toluene (50 ml). Acetic acid (10 ml, 175 mmol) was added and the mixture was heated to reflux (T$_{bath}$=13° C.) overnight. The mixture was transferred into a separatory funnel and a mixture of water/brine (20 ml/30 ml) was added. The phases were separated and the aq. phase was washed with MTBE (30 ml). The org. phases were combined, washed with sat. aq. Na$_2$CO$_3$ (50 ml), brine/water (20 ml/10 ml) and brine (30 ml), dried over MgSO$_4$, filtered and the solvent was evaporated to give ethyl-(4-oxo-4-(2,6,6-trimethylcyclohex-3-en-1-yl)but-2-en-2-yl)cysteinate (8.3 g, 24.5, quant. yield) as a yellow oil.

MS (EI, 70 eV): 339 ([M]$^{+•}$, 4), 216 (94), 174 (100), 142 (65), 116 (42), 107 (27), 84 (41), 67 (36), 58 (39), 41 (33), 29 (67).

Step 2: Ethyl-(4-oxo-4-(2,6,6-trimethylcyclohex-3-en-1-yl)but-2-en-2-yl)cysteinate (3 g, 8.8 mmol) was placed in a 100 ml two-neck round-bottom flask together with (E)-1-(2',6',6'-trimethylcyclohex-3'-en-1'-yl)but-2-en-1-one (1.7 g, 8.8 mmol). Water (50 ml), THF (10 ml) and potassium carbonate (1.2 g, 8.7 mmol) were added and the mixture was stirred at room temperature for three days. The orange mixture was transferred into a separatory funnel, the phases were separated and the aq. phase was washed with MTBE (2×30 ml). The org. phases were combined and washed with water/brine (2×20 ml/10 ml) and brine (20 ml), dried over MgSO$_4$, filtered and the solvent was evaporated to give a yellow oil which was further purified by chromatography (eluent: heptane/MTBE, 8/2) to give ethyl-N-(4-oxo-4-(2',6',6'-trimethylcyclohex-3'-en-1'-yl)but-2-en-2-yl)-S-(4-oxo-4-(2',6',6'-trimethylcyclohex-3'-en-1'-yl)butan-2-yl)cysteinate (1.54 g, 29 mmol, 32.8% yield) as a mixture of isomers and a light yellow oil.

Odor description (dry-down of a 10% DPG solution after 24 hours on a smelling strip): licorice, sweet, damascone.

$^{13}$C-NMR (CDCl$_3$, 100 MHz): δ=211.98, 211.95, 211.93, 211.90, 211.89, 211.84, 200.41, 200.37, 200.35, 170.32, 170.30, 170.28, 170.18, 170.15, 159.97, 159.86, 159.78, 159.72, 159.64, 132.55, 132.51, 131.71, 131.61, 124.17, 124.02, 123.89, 123.85, 100.21, 100.14, 62.81, 62.78, 62.73, 62.72, 62.56, 61.65, 61.63, 56.92, 56.82, 56.76, 56.69, 56.66, 55.28, 55.20, 55.13, 55.09, 55.07, 55.05, 55.01, 42.12, 41.67, 41.65, 41.62, 35.33, 35.26, 35.20, 35.12, 34.35, 34.27, 34.16, 33.97, 33.87 33.82, 33.74, 33.06, 33.04, 32.69, 31.80, 31.67, 31.65, 31.56, 31.53, 31.05, 31.02, 30.04, 30.01, 29.74, 29.69, 28.94, 22.62, 21.98, 21.95, 21.82, 21.77, 21.75, 21.72, 21.59, 21.53, 21.19, 20.66, 20.63, 20.08, 20.04, 19.85, 19.80, 19.34, 19.31, 19.29, 19.27, 14.05, 14.04 ppm.

MS (EI, 70 eV): 408 ([C$_{22}$H$_{34}$NO$_4$S]$^+$, 2), 123 (100), 110 (36), 107 (32), 84 (44), 83 (34), 81 (95), 69 (54), 67 (43), 55 (27), 41 (26).

Example 4: Odor Assessment

|  | Wet | Dry-down after 24 hours | Dry-down after 3 days |
| --- | --- | --- | --- |
| Compound A | Nice, fruity, damascone with a slight plastic note | fruity berry, reminiscent of stewed apple, slightly plastic, chemical | Damascone, fresh |
| Compound B | fruity, damascone, sweet | Fruity, clean, damascone | Fruity, sweet, damascone |
| Compound A + compound B (ratio 1:14) | Damascone, stewed apple, strawberry | fruity, damascone like, stewed apple, clean, pleasant | damascone |

Compound A: Ethyl S-(4-oxo-4-(2',6',6'-trimethylcyclohex-3'-en-1'-yl)butan-2-yl) cysteinate Compound B: Ethyl N,S-bis(4-oxo-4-(2',6',6'-trimethylcyclohex-3'-en-1'-yl)butan-2-yl)cysteinate)

As can be seen from the odor description above, when combining the compound of formula (I) with a compound of formula (III) the plastic note disappeared.

Example 5: Fragrance Comprising a Compound of Formula (I)

| Compound/Ingredient | parts by weight 1/1000 |
|---|---|
| 2-methyl-1-phenylpropan-2-yl acetate | 20 |
| 4-(tert-butyl)cyclohexyl acetate | 50 |
| (2-(1-ethoxyethoxy)ethyl)benzene | 2 |
| AGRUMEX (2-(tert-butyl)cyclohexyl acetate) | 25 |
| 2-phenylethan-1-ol | 10 |
| (E)-2-benzylideneoctanal | 100 |
| 2-methylundecanal | 1 |
| AMBROFIX (3a,6,6,9a-tetramethyldodecahydronaphtho[2,1-b]furan) | 1 |
| methyl 2-aminobenzoate | 2 |
| AUBEPINE PARA CRESOL (4-methoxybenzaldehyde) | 3 |
| lemon terpens | 10 |
| Citronellol | 80 |
| delta damascone | 2 |
| DIHYDRO MYRCENOL | 100 |
| DIPHENYL OXIDE | 10 |
| DUPICAL (4-(octahydro-5H-4,7-methanoinden-5-ylidene)butanal) | 2 |
| EUCALYPTOL NATUREL | 3 |
| FLOROCYCLENE (3a,4,5,6,7,7a-hexahydro-1H-4,7-methanoinden-6-yl propionate) | 75 |
| GARDENOL (1-phenylethyl acetate) | 20 |
| ISO E SUPER | 100 |
| ISORALDEINE | 25 |
| JAVANOL @ 10% DPG | 5 |
| LEMONILE (3,7-dimethylnona-2,6-dienenitrile) | 2 |
| METHYL ACETOPHENONE (1-(p-tolyl)ethan-1-one) | 2 |
| 4-(tert-butyl)cyclohexan-1-ol | 10 |
| PATCHOULI ESS SANS FER INDONESIE ORPUR | 3 |
| PHARAONE (2-cyclohexylhepta-1,6-dien-3-one) 10%/DPG | 5 |
| Hexyl salicylate | 75 |
| SERENOLIDE (2-(1-(3,3-dimethylcyclohexyl)ethoxy)-2-methylpropyl cyclopropanecarboxylate) | 30 |
| SPIROGALBANONE (1-(spiro[4.5]dec-6/7-en-7-yl)pent-4-en-1-one | 1 |
| STEMONE ((Z)-5-methylheptan-3-one oxime) | 1 |
| TETRAHYDRO LINALOL | 50 |
| UNDECAVERTOL | 10 |
| Dipropylen glycol (DPG) | 165 |
| Total: | 1000 |

The fragrance composition above is a fresh floral green accord, reminiscent of fresh green muguet. This fragrance can be applied, e.g. in high density liquid detergent (HDLD, at 0.1-1.5 wt % (e.g. 0.6 wt %).

By replacing 45 parts of DPG of the accord above by a mixture of ethyl S-(4-oxo-4-(2',6',6'-trimethylcyclohex-3'-en-1'-yl)butan-2-yl) cysteinate and ethyl N,S-bis(4-oxo-4-(2',6',6'-trimethylcyclohex-3'-en-1'-yl)butan-2-yl)cysteinate (ration about 1:14), the overall character is now softer, fruitier, reminiscent of stewed apple on dry fabric. The fresh fruitiness is clearly enhanced over time, and last for several days.

By replacing 55 parts of DPG of the accord above by a mixture comprising ethyl S-(4-oxo-4-(2',6',6'-trimethylcyclohex-3'-en-1'-yl)butan-2-yl) cysteinate (2.7 parts), ethyl N,S-bis(4-oxo-4-(2',6',6'-trimethylcyclohex-3'-en-1'-yl)butan-2-yl)cysteinate (37.3 parts), and one additional precursor (4-(dodecylthio)-4-methylpentan-2-one (15 parts)), a very unusual and pleasant effect is the overall lift and radiance of the perfume on the dry fabric; with this combination the fresh fruitiness is not only enhanced and prolonged, but it furthermore has an enhanced volume and lift.

Example 6: Precursor Deposition Studies on Cotton in Heavy Duty Liquid Detergent Application A liquid detergent composition (4.0 mg) was prepared with unperfumed heavy duty liquid detergent (HDLD) base containing 0.2% wt/wt of a mixture of Example 2. This liquid detergent composition was dissolved in 1 L of cold tap water to produce a wash liquor containing precursor. The wash liquor (100 mL) was placed in a 150 mL conical flask together with 2 cotton pads (10×10 $cm^2$, each weighing 2.5 g). The flask was closed with a screwcap and shaken on a thermostated shaking table at 200 rpm and 40° C. for 1 h. The liquids were discarded and the cotton pads wrung out (wet weight 4.5 g) and put back in the conical flasks. After adding 75 mL of cold tap water, rinsing was effected by shaking for 30 min at RT. The cotton pads were wrung out and extracted with an accelerated solvent extractor ($CH_3CN$, 60° C., 1500 psi), and the extracts (15-20 ml, precisely determined) were submitted to quantitative analysis by HPLC. The above process was repeated, with the difference that the towels were extracted after a period of 24 h line dry in ambient air.

The above two processes were repeated with liquid detergent composition containing 0.2% of 6-Damascone instead of the mixture of Example 2.

The quantification of 6-Damascone as such and the precursors thereof in the cotton pad extracts was effected by HPLC-UV with external calibration (0.3-20 ppm) of the reference materials in $CH_3CN$. The results are shown in the Table below.

| HDLD | Mixture of Example 2 (δ-Damascone precursor + released δ-Damascone) | δ-Damascone (comparison) |
|---|---|---|
| wet | (9 + 2)% | 6% |
| 24 h line dry | (6 + 1)% | 0.7% |

The results show that the mixture of Example 2, which contains a mixture of bis- and mono adduct, leads to the release of a perceivable amount of δ-Damascone already on the wet stage. After 24 h line drying, the amount of δ-Damascone delivered from the precursor has exceeded the amount when using free δ-Damascone. In addition, a large reservoir of precursor is available for continued long lasting release of the odorant. Overall, the amount of bound and free δ-Damascone delivered from the precursor on dry fabric is over 5 times bigger than when using free δ-Damascone. The results suggest also that a combination of free δ-Damascone and precursor may produce advantageous effects.

Example 7: Precursor Deposition Studies on Cotton in Heavy Duty Liquid Detergent Application Example 6 was repeated replacing the unperfumed heavy duty liquid detergent base with an unperfumed fabric conditioner base. The application involved a single cycle of shaking at 200 rpm at room temperature for 20 min, following by wringing out the cotton pads and ASE (accelerated solvent extractor) extraction.

The quantification of 5-Damascone as such and the precursors thereof in the cotton pad extracts was effected by HPLC-UV with external calibration (0.3-20 ppm) of the reference materials in $CH_3CN$. The results are shown in the Table below.

| Fabric conditioner | Mixture of Example 2 (δ-Damascone precursor + released δ-Damascone) | δ-Damascone (comparison) |
|---|---|---|
| wet | (43 + 7)% | 14% |
| 24h line dry | (34 + 1.3)% | 1.1% |

The results show that the mixture of Example 2, which contains a mixture of bis- and mono adduct, leads to the release of a perceivable amount of δ-Damascone already on wet stage. After 24 h line drying, the amount of δ-Damascone delivered from the precursor had slightly exceeded the amount when using free δ-Damascone. Overall, the amount of bound and free δ-Damascone delivered from the precursor on wet fabric was 2.6 times higher than when using free δ-Damascone and over 25 times bigger on dry fabric. The results suggest also that a combination of free δ-Damascone and precursor may produce advantageous effects.

The invention claimed is:

1. A detergent or fabric conditioner comprising a compound of formula (I)

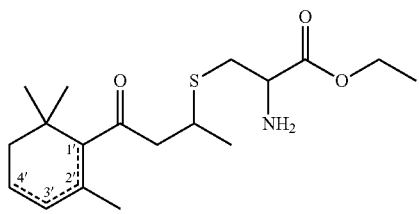

(I)

in which one of the dotted lines represents together with the carbon-carbon bond a double bond and each of the other two dotted lines represent together with the carbon-carbon bond a single bond,
and a compound of formula (III)

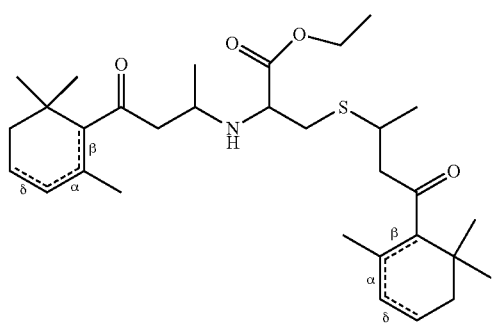

(III)

wherein the dotted lines represent a double bond located at one of the alpha-, beta- or delta- positions on each of the cyclohexene rings.

2. The detergent or fabric conditioner of claim 1 comprising the compound of formula (I) and the compound of formula (III) in a ratio of 1:40 to 40:1.

3. The detergent or fabric conditioner of claim 2, wherein the compound of formula (I) is ethyl S-(4-oxo-4-(2',6',6'-trimethylcyclohex-3'-en-1'-yl) butan-2-yl) cysteinate and the compound of formula (III) is ethyl N,S-bis(4-oxo-4-(2',6',6'-trimethylcyclohex-3'-en-1'-yl) butan-2-yl) cysteinate.

4. The detergent or fabric conditioner of claim 1 further comprising a compound of formula (IV)

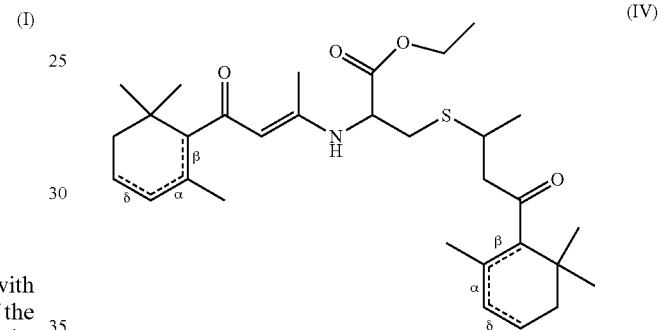

(IV)

wherein the dotted lines represent a double bond located at one of the alpha-, beta- or delta-positions on each of the cyclohexene rings.

5. The detergent or fabric conditioner of claim 4, wherein the compound of formula (IV) is ethyl N-(4-oxo-4-(2',6',6'-trimethylcyclohex-3'-en-1'-yl) but-2-en-2-yl)-S-(4-oxo-4-(2',6',6'-trimethylcyclohex-3'-en-1'-yl) butan-2-yl) cysteinate.

* * * * *